US009500568B1

(12) United States Patent
Wise

(10) Patent No.: US 9,500,568 B1
(45) Date of Patent: Nov. 22, 2016

(54) INFLATABLE INLET FOR AEROSOL SAMPLING

(71) Applicant: U.S. Army Edgewood Chemical Biological Center, APG, MD (US)

(72) Inventor: Daniel G. Wise, Ellicott City, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 626 days.

(21) Appl. No.: 13/770,630

(22) Filed: Feb. 19, 2013

(51) Int. Cl.
*G01N 1/00* (2006.01)
*G01N 1/22* (2006.01)

(52) U.S. Cl.
CPC .................................. *G01N 1/2202* (2013.01)

(58) Field of Classification Search
CPC .................. G01N 2001/2223; G01N 1/2202; G01N 1/24; G01N 2001/022; G01N 2001/025
USPC ...................................................... 73/864.33
See application file for complete search history.

(56) References Cited

U.S. PATENT DOCUMENTS

| | | | | | |
|---|---|---|---|---|---|
| 2,701,559 | A * | 2/1955 | Cooper | A61B 10/02 | 15/104.33 |
| 5,040,424 | A * | 8/1991 | Marple | G01N 1/2205 | 73/863.23 |
| 6,322,230 | B1 * | 11/2001 | Medici | F21S 9/022 | 340/321 |
| 6,584,865 | B1 * | 7/2003 | Doherty | G01N 1/2202 | 73/863.03 |
| 7,543,478 | B2 * | 6/2009 | Burroughs | G01N 1/2202 | 73/28.01 |
| 7,690,276 | B1 * | 4/2010 | Wise | G01N 1/2202 | 73/864.33 |
| 8,429,987 | B1 * | 4/2013 | Linker | G01N 1/22 | 73/864.33 |
| 8,684,327 | B2 * | 4/2014 | Caswell | F16M 11/24 | 248/168 |
| 2003/0136203 | A1 * | 7/2003 | Yoon | A61L 2/00 | 73/864.33 |
| 2004/0043443 | A1 * | 3/2004 | Lejeune | G01N 1/2273 | 435/29 |
| 2004/0118222 | A1 * | 6/2004 | Cornish | G01N 1/2252 | 73/863.22 |
| 2006/0060006 | A1 * | 3/2006 | Ornath | G01N 1/22 | 73/864.33 |
| 2008/0106888 | A1 * | 5/2008 | Nalitchaev | F21S 8/083 | 362/96 |
| 2009/0114294 | A1 * | 5/2009 | Wallace | F17C 13/04 | 137/561 R |
| 2011/0232498 | A1 * | 9/2011 | Novosselov | B01D 45/06 | 96/413 |
| 2011/0257922 | A1 * | 10/2011 | Fang | G01N 1/2273 | 702/100 |
| 2012/0004571 | A1 * | 1/2012 | Ku | A61B 5/082 | 600/562 |
| 2014/0180156 | A1 * | 6/2014 | Ku | G01N 1/2205 | 600/532 |
| 2014/0377066 | A1 * | 12/2014 | Anderson | F03D 1/065 | 416/44 |

* cited by examiner

*Primary Examiner* — Peter Macchiarolo
*Assistant Examiner* — Mohammed E Keramet-Amircolai
(74) *Attorney, Agent, or Firm* — Ulysses John Biffoni

(57) ABSTRACT

The present invention is directed to an air intake for an aerosol sampling device, the air intake being inflatable and deflatable.

20 Claims, 5 Drawing Sheets

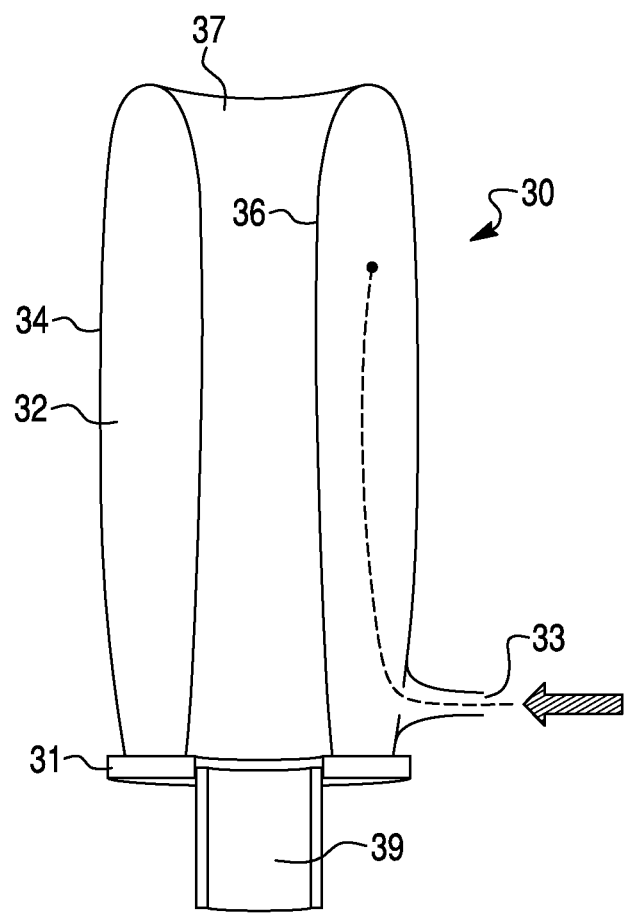

INFLATABLE INLET FOR AEROSOL SAMPLING

The invention described herein may be manufactured, used and licensed by or for the United States Government.

FIELD OF THE INVENTION

The present invention relates to air sampling and, in particular, sampling of air that contains aerosol particles. More specifically, the invention is directed to aerosol sampling situations where storage and remote or automatic deployment of aerosol sampling devices are required.

BACKGROUND OF THE INVENTION

Aerosols consist of small particles, liquid or solid, that are suspended in air. Airborne dust particles, virus particles and bacteria can also comprise an aerosol.

The study of aerosols has significance in many areas such as environmental and health studies, Homeland Security, and military defense, especially when the aerosol particles are pathogens. The device for collecting aerosol particles, commonly known as an aerosol sampler, is a critical component for these studies; its function is to collect aerosol-containing air and to characterize the concentration and type of the aerosol particles contained in the air.

Aerosol particles entrained in moving air have mass and velocity vectors—i.e., they have momentum—as they are collected for sampling. Because of their mass, aerosol particles have inertia; they resist changes in their velocity vectors as their paths carry them into and through sampling collectors.

In a typical aerosol sampler, the aerosol-containing ambient air is first aspirated into the air sampler system through the air intake or inlet and thence transmitted to the rest of the sampler, sometimes through a system of transmission tubes or ducts, so as to convey the aerosol-containing air sample to the measurement portion of the aerosol-sampling device.

One of the basic performance parameters for an aerosol sampler is sampling efficiency. Overall sampling efficiency ($\eta_0$) is the ratio of amount of aerosol material in the collected sample ($C_{coll}$) to the amount of aerosol in the air ($C_{air}$) being sampled. It is usually calculated as the ratio of particles collected per volume of air sampled to the concentration (C) of particles in the ambient air.

$$\eta_0 = Cc_{oll}/C_{air}$$

The goal of unbiased aerosol air sampling is to measure the actual amount of aerosol, measured as the number of aerosol particles or as the weight of the airborne aerosol material, in an air sample that is as representative as possible of the air being sampled.

Aerosol air sampling often takes place in windy settings, wherein the sampled air has to be pulled from horizontal flow into a vertically oriented air intake. Because of the inertial aspects of aerosol particles, the change in direction from horizontal to vertical can cause a portion of the massive aerosol particles to overshoot the air intake and, also, to impact against, and lodge upon, the walls of the air intake sampling tube.

Therefore, a goal of aerosol air sampling is to collect air samples in such a way that $\eta_0$ is as close to 1 as possible, regardless of wind direction and speed or particle size. It may also be desirable for $\eta_0$ to be greater than 1 if one wants to maximize the amount of aerosol collected. A high-efficiency air intake is one that is resistant to the influence of wind upon collecting efficiency. A high efficiency air intake is important for the gathering of reliable aerosol air sampling data.

Although air intakes or inlets for aerosol sampling devices can be very complex, in general, they are simple structures that typically consist of a pipe or stack that extends a distance upwards from the aerosol sampler to a debris/rain hat or cap/shell with an annular air intake opening. Many situations require that the opening of the inlet be distanced from the rest of the sampler enclosure to assure the aerosol sample is taken from an appropriate sampling height, or that it is taken from air that is not adversely affected by the flow around the enclosure or emissions from the sampler itself. This means that inlets for outdoor air sampling can range from several inches in height to over 6-feet above the sampler enclosure. As the inlet usually protrudes well above the aerosol sampler, it makes movement of the sampler awkward; therefore, the inlet is usually detachable and removed. In sampling in hazardous environments, the sampling crews may risk prolonged and unhealthful exposure if such crews need to attach and/or detach inlets for aerosol sampling.

SUMMARY OF THE INVENTION

The concept of this invention is an inflatable inlet for aerosol sampling that is made from a flexible airtight material such as coated fabric or vinyl, and the structure and shape of the inlet is maintained by inflating the inlet material. An inflatable inlet may remain attached at all times, where it can be deployed or stowed remotely by supplying pressurized gas to the inflatable structure.

Many advantages could be gained by an inflatable inlet for an aerosol sampling device. As the inlet for such device usually protrudes well above the aerosol sampler, the extended inlet makes movement of the sampler awkward. Moreover, aerosol sampling requires that sampling be performed while the sampling inlet is stationary due to the general ineffectiveness of uni-directional inlets in moving air streams, and the practical concern that rigid inlets may hit low hanging objects when the system is on the move. Accordingly, the inlet is usually detachable and removed from the sampler. The inflatable inlet of this invention does not need to be removed when the sampler is being moved. The inflatable inlet can remain in place atop the sampler and would self-deploy when the sampler operates and self-stow when the sampler is inactive. A specific example of where this would be very helpful is in sampling in hazardous environments where the sampling crew is at risk, as noted above, if they need to attach and/or reattach an inlet to the sampling system while a hazard exists.

BRIEF DESCRIPTION OF THE DRAWINGS

FIG. 1 is a schematic illustration of a movable sampling device containing an attachable inlet, as in the prior art.

FIG. 2A is a schematic of a movable aerosol sampling device containing the inflatable inlet of the present invention in the deflated condition.

FIG. 2B is a schematic of a moveable aerosol sampling device of FIG. 2A, in which the inflatable inlet is in the inflated condition.

FIG. 2C is a schematic of a simple version of the inflatable inlet

FIGS. 3A, 3B and 3C is a schematic of the inflatable inlet of this invention being in a deflated state, a semi-inflated state and a full inflated state, respectively.

DETAILED DESCRIPTION OF THE INVENTION

"Aerosol" is defined herein as a dispersion of solid and liquid particles suspended in gas, including virus particles and bacteria.

'Eduction' is defined herein as the tendency of a flow of a high speed primary fluid to entrain a secondary fluid adjacent to the primary flow. The mechanism of eduction derives from the primary flow's momentum being transferred to the stagnant adjacent fluid through turbulent mixing of the primary flow with the adjacent fluid, thereby inducing a secondary flow which is pulled downstream by turbulent shear forces. 'Educted' flow refers to fluid motions imparted to ambient fluids by a fluid jet"

"Air intake" refers to the basic invention described herein. It is an air intake for an aerosol sampling device. The terms "inlet," "air intake probe" and "intake probe" refer to the actual air inlet tube through which aerosol-laden air is drawn for analysis. The "inlet probe" is contained within the air intake and is generally concentric with it.

Figure 1:
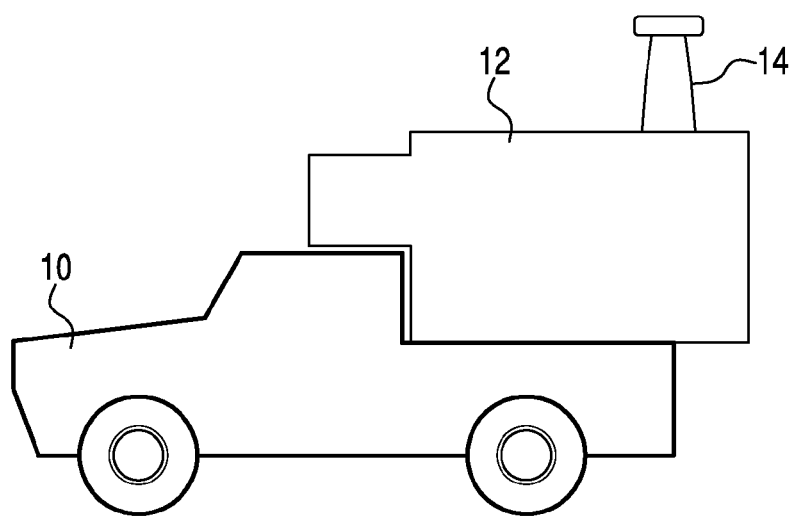

This invention is particularly useful when aerosol sampling needs to be taken along a wide area and, the sampling needs to be taken in hazardous environments, where the sampling personnel is at risk if such personnel needs to be outside in the hazardous environment to attach an inlet to the sampling system. While the invention is not to be limited, the invention is particularly useful in providing sampling systems in mobile vehicles. This situation can easily occur in military operations, where sampling of bio-hazards is currently done from shelters located in tactical vehicles (e.g. Joint Biological Point Detection System-JBPDS). A schematic example of such a vehicle 10 is shown in FIG. 1. Currently, sampling crews must leave the safety of shelter 12, on vehicle 10, to deploy the sampling inlet 14. As noted previously, operations for point detection systems, such as, but not only the JBPDS, require that sampling be performed while vehicle 10 is stationary. This is due to several reasons, including the general ineffectiveness of uni-directional inlets in the moving airstreams, and that protruding sampling inlets may hit low hanging objects while vehicle 10 is on the move. However, in the present invention, the sampling inlet is an inflatable structure, allowing the sampling inlet to be deployed from the interior of the tactical vehicle. Once sampling is completed at the desired location, the sampling inlet can be deflated, again, from inside the vehicle and the vehicle moved with the sampling inlet in a deflated condition to an additional area to be sampled.

Figure 2A:
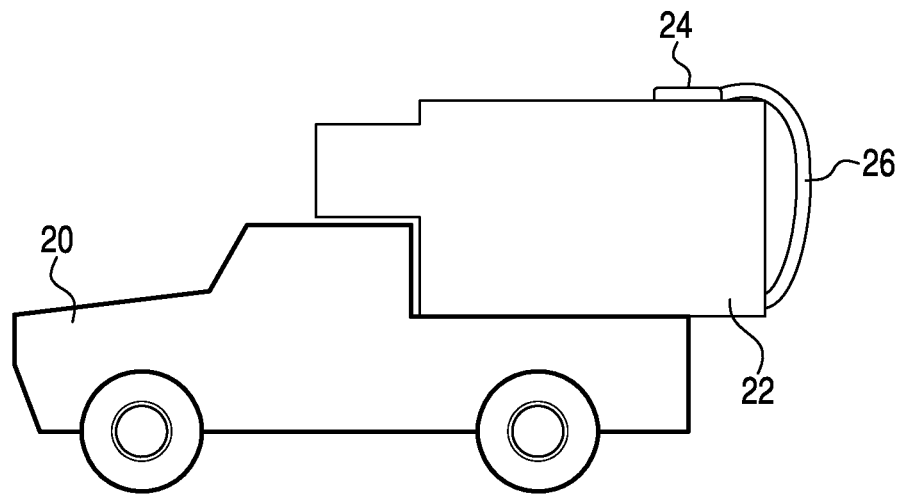
Figure 2B:
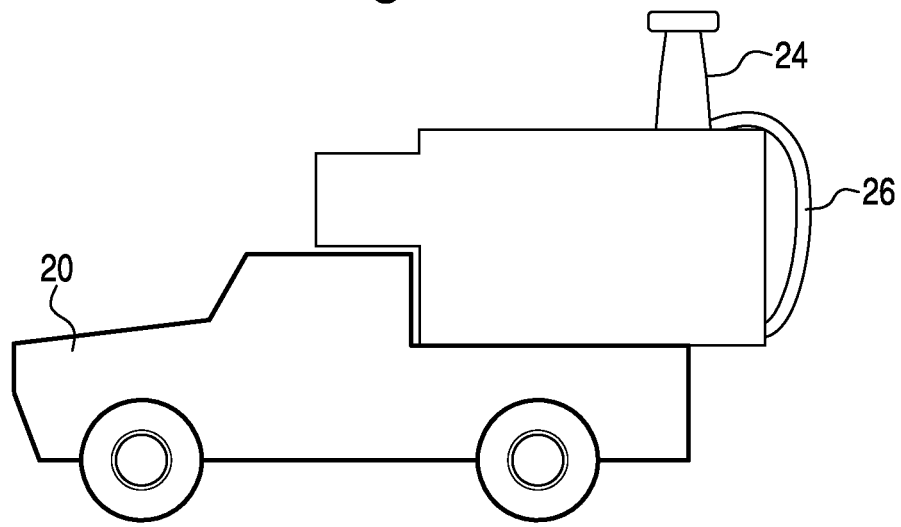

FIG. 2A shows a vehicle 20 with a shelter 22 thereon, containing a sampling system (not shown), which contains an inflatable sampling inlet 24, which is in communication with the system used to analyze the aerosol being sampled. FIG. 2B illustrates in schematic fashion, vehicle 20, containing the inflated sampling inlet 24. Inlet 24 is inflated by a compressed air source (not shown), and which directs air through hose or piping 26 into inflated inlet 24. It is to be understood that while the inflatable sampling inlet of this invention is particularly useful for mobile systems in detecting and analyzing airborne particles, the inflatable inlet of this invention also has use in stationary sampling systems.

If the inflatable inlet structure of this invention is configured as an air amplifying educator as in U.S. Pat. No. 7,690,276, then the pressurized gas that inflates the structure can also be used to entrain a large volume of sample-containing air through the inlet. This will result in a very high efficiency (enriching) inlet that samples in an omni-directional fashion with an aspiration efficiency that is insensitive to wind speed. The entire content of U.S. Pat. No. 7,690,276 is herein incorporated by reference.

According to the invention described in U.S. Pat. No. 7,690,276, there is disclosed an apparatus for redirecting a flow of aerosol-containing air, comprising an air intake disposed within the flow of aerosol-containing air, a structure for redirecting a portion of the flow of aerosol-containing air into the air intake, and a sampling tube having an opening for receiving aerosol-containing air disposed within the air intake. Further, the structure for redirecting a portion of the flow of aerosol-containing air into the air intake comprises a source of pressurized gas, and a structure for injecting the pressurized gas into the air intake so as to cause the flow of the portion of aerosol-containing air in the air intake.

Figure 3A:
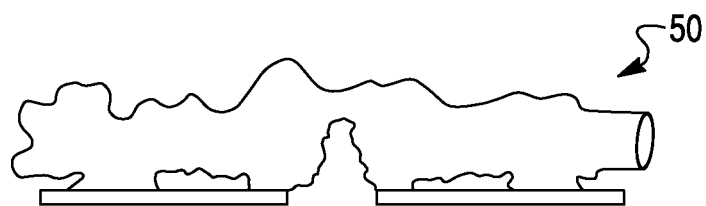
Figure 3B:
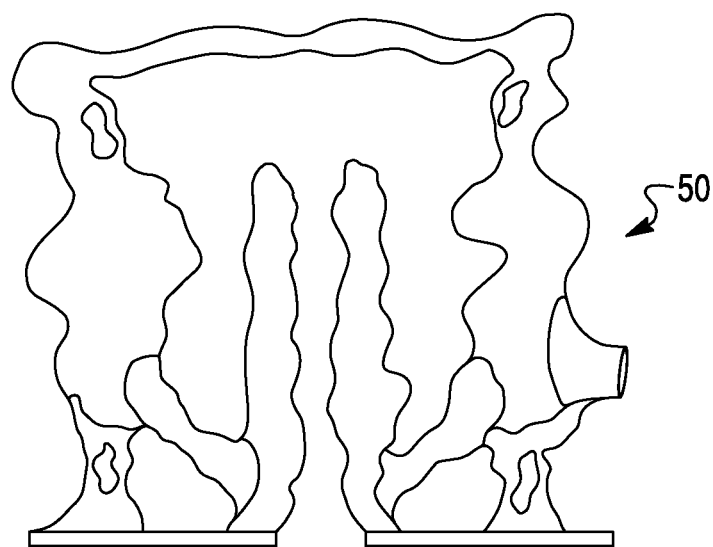
Figure 3C:
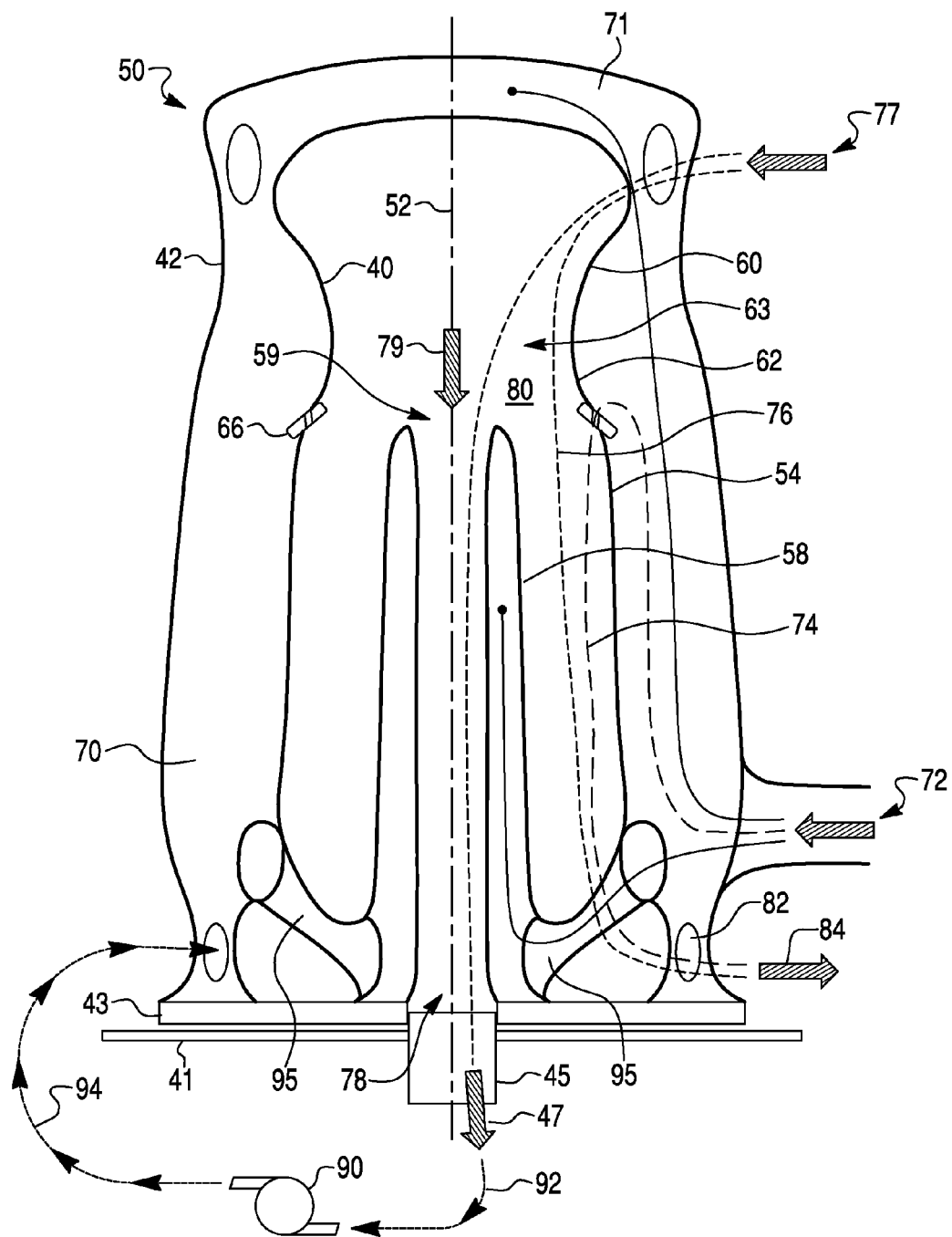

FIG. 3C is a schematic view of an air intake system 50, which can be inflated according to the present invention. Air intake 50, as shown, is described in afore-mentioned U.S. Pat. No. 7,690,276, with the improvement of this invention that air intake 50 is inflatable and can be deflated for transport and/or ease of use. It is to be understood that the present invention is not to be strictly limited to the structure of air intake 50, as shown in FIG. 3C herein, but that the concept of this invention is directed to any air intake system for an aerosol sampling device that is inflatable and can be deflated after use at a specific designation.

For example, FIG. 2C illustrates a simple concept of the inflatable inlet. As shown therein, the inflatable air intake 30 is simply formed from a cylindrical annular manifold 32, enclosed by outer wall 34 and inner wall 36. The manifold 32 is pressurized from inlet 33, which is connected to a source of pressurized gas (not shown). The air intake 30 can be attached to a rigid base 31, which itself can be attached to any moveable or stationary structure. Environmental air which is to be tested for sampling of any particles therein is directed into the cylindrical inlet 37, which is formed within the interior of annular manifold 32. The sampled air is directed from inlet 37 to the inlet 39 of an aerosol sampler (not shown).

The air intake system 50 as shown in FIG. 3C, is comprised of an inner shell 40 and outer shell 42, which form an annular manifold 70, which includes a top cap 71, and that are pressurized by an external gas source through inlet port 72. If these inner and outer shells 40 and 42 are fabricated from flexible airtight material, then an inflatable structure is possible, whereas the gas flow into the inlet port 72 will pressurize the manifold 70 and transform intake system 50 into a standing inflated structure. The air intake system 50 includes an inner pathway 63 that is approximately circular in shape about a vertically oriented central longitudinal axis 52 extending there through. The inner pathway 63 includes three primary sections; a converging portion 60, a cylindrical section 62, and a diverging section 54, which also serves as an outlet for the redirected airflow.

The converging portion 60 of, air intake 63 has a curved shaped surface formed according to a curve rotation. The curve being of the set of curves that includes circles and parabolas. The gently curving inlet portion 60 converges with the cylindrical portion 62 to form a smooth surface so as to minimize the onset of turbulent flow within and downstream of the central flow region 80. The diverging portion 54 of the air intake 63 diverges from the central longitudinal axis 52 with an angle of preferably about 3.5 degrees. It is, however, within the scope of the present invention that the angle of divergence can be 0 degrees, i.e., the cylindrical portion 62 of the air intake 63 can continue to extend downward and effectively form an extension of the circular cylinder portion 62.

An air inlet sampling tube 58 is disposed, preferably concentrically within diverging portion 54 and has an intake opening 59 disposed at the same level or just above the bottom end of the cylindrical portion 62 of the air intake 63. The opposite end 78 of the air inlet sampling tube 58 is connected to an aerosol sampler, not shown. Air intake system 50 can be secured to the metal shelter roof 41 of a vehicle (not shown) via a magnetic ring 43. Air flow through sampling tube 58 is directed to the aerosol sampler via inlet pipe 45, as shown by arrow 47.

Manifold 70, that can be concentric with the vertical longitudinal axis 52, has a rigid annular nozzle 66, located at the entrance to the diverging portion 54. The annular manifold 70 can be connected to a supply of eduction-driving air 74 by way of a supply of pressurized gas indicated by arrow 72, and as described herein below. These components form what is known as a "Coanda-type" eductor.

The source of pressurized gas to drive the eduction effect in many commercial applications is generally a portable air compressor. However, in biological or environmental sampling applications as contemplated with respect to the present invention, this educting air flow may be readily supplied on a sampler's mounting platform, e.g., engine exhaust from the tactical vehicle described above (although contamination of the sampled air may be a concern in this scenario). Steam from naval vessels may be an alternative pressurized gas source. Advantageously, the intake 50 can be configured such that the pressurized gas to drive the eduction effect (the motive gas), also inflates intake 50. Thus, intake 50 can be prepared such that pressurized gas enters 50 through port 72 and inflates the intake 50 structure. This same pressurized gas is the source of the eduction air 74, which exits nozzle 66 (creating a backpressure that allows the intake structure 50 to remain pressurized and hence inflated). This exiting flow is indicated by arrow 74 and is mixed with diverted aerosol-containing gas 76 and exits the inner pathway 63 of intake 50 through ports 82 as indicated by arrow 84. The air inlet sampling tube 58 can be configured to likewise inflate through strut-ports 95 which communicate with the same inflation gas and pressure that maintains the inflation of manifold 70.

Likewise, it is possible to attach one or more spaced rings or other attachment means between sampling tube 58 and the inner wall 40 of manifold 70, such that as manifold 70 inflates, sampling tube 58 will rise. Again, the exact configuration of air intake system 50 is not critical to this invention, only that the air intake system be provided that will inflate with a pressurized gas source. Once pressurized gas flow via arrow 72 is stopped, air can escape the inflated system, shown in FIG. 3C, via nozzle 66.

FIGS. 3A and 3B show the air intake system 50 in a completely deflated state, and partially inflated state, respectively.

It is also within the terms of the present invention to use an alternative source of pressurized gas: i.e., reuse the energy already existing in the exhaust flow of the aerosol air sampler upon which the present invention is to be used. Again, referring to FIG. 3C, most aerosol air samplers use a blower 90 to draw air through the inlet and sampling system, as indicated by reference arrows 47 and 92, and the exhausted air, indicated by reference arrows 94, still has sufficient kinetic energy for use as to drive the eduction effect, and inflate intake 50 and maintain intake 50 in an inflated state.

If properly engineered, such use of the exhausted gas from the air sampler will have little effect on the flow rate through the sampler. It is therefore within the terms of the present invention for the exhaust of the sampler, or a portion of the exhaust, to be re-routed to the annular manifold 70, by means of air supply 72, which communicates between the manifold and the exhaust of the air sampler. This should be feasible if the pressure drop in the annular nozzle 66 is low so that it does not load the blower and reduce the primary flow, which passes through the sampling system.

While the eduction method of pumping air can be achieved in an efficient way by injecting a curtain of gas from the annular opening of nozzle 66, it is within the terms of the invention that the eduction can also be achieved by the injection of pressurized gas from a one or more single circular nozzles into the flow of diverted aerosol-containing gas 76. In other words, the injection of a single jet of gas into the air intake 63 can transfer momentum to, and entrain, another gas, such as air, and, by the eduction process, cause air to move in the duct.

The overall result of eduction is a large increase in the volume flow rate of the inlet air by means of the use of a small volume of fast-moving air-in effect, a flow amplifier. The advantage of using the eduction effect in the present invention is that it initiates and maintains the aerosol flow from the environment through port 81 in manifold 70, as indicated by the arrow 77, in FIG. 3C, without requiring the use of a large blower on the actual inlet region bounded by inner and outer walls 40 and 42. This method of inducing a gentle redirection of the horizontal wind-driven airflow into a vertical flow minimizes inertial losses of particles such that the concentration of air-entrained aerosol particles is minimally affected by the changed direction of the air that is sampled. The eduction force which draws the air can easily overpower the ambient wind force and therefore eliminate or severely mitigate the wind sensitivity of aerosol air samplers.

To summarize the basic concept: this aerosol sampling air intake device 50 uses eduction to redirect ambient air containing aerosol particles towards a directional sampling probe which is oriented in the direction of air flow through an air intake device 50. The eduction zone is vertically oriented so that it aspirates, in an omni-directional fashion, large volumes of the ambient air.

In the operation of air intake system 50, aerosol containing air to be sampled, as indicated by the arrows 77 of FIG. 3C, is drawn into the inner pathway 63 by means such as the method of the aforementioned eduction. That is, the manifold 70 directs pressurized gas into annular nozzle 66. The pressurized gas is directed from the same height or below the inlet opening 59 and in the direction past the sampling tube 58 to create a curtain of fast-moving air that is discharged through the annular nozzle 66 as an annular sheet of air moving in a downward direction. The aerosol-containing air 77 is drawn into the inner pathway 63 by the curtain of fast-moving pressurized gas. Then the air that is captured in the inner pathway 63 moves downward towards the air sampling tube 58 and into inlet or opening 59 at the upper most location through which sampled gases (indicated, roughly, by the arrows 79) are captured for delivery from outlet 78 into the air sampling machine (not shown).

It can now be appreciated that the air intake apparatus 50, shown in FIG. 3C, enables the redirecting of horizontal airflow into a downward-directed flow in such a way as to make a gentle turn from the horizontal plane where the wind is a variable to a vertical direction where the downward-directed flow has a constant direction and relatively constant velocity parallel to the vertically oriented axis of the air intake 50.

The air intake system 50, thus far described, combines the enhanced inlet efficiency of a directional sampling probe inlet with the wind direction insensitivity of the prior art omni-directional inlet that comprises part of the method of achieving improved sampling efficiency. This will allow high efficiency, aerosol sampling from moving air from any direction without the need to articulate an inlet tube of an air intake device such that its axis is in approximate alignment with the prevailing wind-velocity vector. Since the wind vector variables exist mostly in a generally horizontal plane, omni-directional inlets are oriented vertically to maximize sampling efficiency and uniformity in conditions of wind from any direction. By orienting the inlet vertically however, the flow must be turned 90 degrees downward, as should be apparent to those who are skilled in the art.

Although the invention has been shown and described with respect to a certain preferred embodiment or embodiments, certain equivalent alterations and modifications will occur to others skilled in the art upon the reading and understanding of this specification and the annexed drawings. In particular, regard to the various functions performed by the above described air intake device for aerosol sampling systems, the terms (including a reference to a "means") used to describe such device are intended to correspond, unless otherwise indicated, to any device which performs the specified function of the described device (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

The invention claimed is:

1. An air intake for an aerosol sampling device, said air intake capable of being inflated by a source of pressurized gas and capable of deflating when said source of pressurized gas is stopped, and said air intake including an inlet for receiving an aerosol from the environment, and an outlet spaced from said inlet for directing aerosol from said inlet to said aerosol sampling device.

2. The air intake of claim 1, including an inlet sampling tube spaced from said inlet and in communication with said outlet.

3. The air intake of claim 2, wherein said sampling tube is capable of inflating and deflating when said air intake inflates and deflates.

4. The air intake of claim 3, wherein said air intake further includes a converging inlet portion from said inlet, a intermediate cylindrical portion downstream from said inlet portion and a diverging portion downstream from said cylindrical portion, an annular conduit disposed adjacent to the diverging portion, said annular conduit having a conduit inlet for receiving said source of pressurized gas and a conduit outlet for directing an annular sheet of said pressurized gas into the diverging section past the inlet of said sampling tube.

5. The air intake of claim 4, wherein the inlet of said sampling tube is disposed within or downstream of mid cylindrical portion.

6. The air intake of claim 4, wherein pressurized gas entering the inlet of said annular conduit is capable of inflating said air intake.

7. The air intake of claim 4, attached to a vehicle.

8. The air intake of claim 7, wherein said source of pressurized gas is the exhaust from said vehicle.

9. The air intake of claim 4, wherein the source of pressurized gas is from the exhaust of an air sampling device.

10. The air intake of claim 1, attached to a vehicle.

11. The air intake of claim 10, wherein said source of pressurized gas is an exhaust from said vehicle.

12. The air intake of claim 1, wherein said source of said pressurized gas is a blower exhaust, said blower capable of drawing air through said inlet and into said sampling system from said outlet.

13. The air intake of claim 2, including a manifold spaced from and surrounding said inlet sampling tube.

14. The air intake of claim 13, including a cover spaced from and over said inlet sampling tube, said cover comprising a portion of said manifold.

15. The air intake of claim 13, wherein said inlet for receiving an aerosol from the environment includes ports through said manifold.

16. The air intake of claim 15, wherein said ports are placed in or adjacent to said cover.

17. The air intake of claim 13, wherein said manifold communicates with said inlet sampling tube such that said pressurized gas source inflates said manifold and said inlet sampling tube.

18. The air intake of claim 13, containing outlet ports through said manifold to allow said air intake to deflate said air intake.

19. The air intake of claim 13, wherein said manifold is attached to a magnetic support.

20. The air intake of claim 19, wherein said magnetic support is attached to the roof of a vehicle.

* * * * *